(12) United States Patent
Tappehorn et al.

(10) Patent No.: US 8,316,845 B2
(45) Date of Patent: Nov. 27, 2012

(54) DEVICE FOR RELEASING BREATHING GAS

(75) Inventors: Ludger Tappehorn, Stockelsdorf (DE); Klaus Abraham, Lübeck (DE)

(73) Assignee: Dräger Medical GmbH, Lübeck (DE)

( * ) Notice: Subject to any disclaimer, the term of this patent is extended or adjusted under 35 U.S.C. 154(b) by 1093 days.

(21) Appl. No.: 12/241,147

(22) Filed: Sep. 30, 2008

(65) Prior Publication Data

US 2009/0114225 A1 May 7, 2009

(30) Foreign Application Priority Data

Nov. 7, 2007 (DE) .......................... 10 2007 052 898

(51) Int. Cl.
*A61M 11/00* (2006.01)
(52) U.S. Cl. ............... 128/202.27; 128/205.24
(58) Field of Classification Search ............ 128/204.18, 128/205.24, 205.25, 202.27, 206.12, 206.15–206.21, 128/206.26, 207.12, 912
See application file for complete search history.

(56) References Cited

U.S. PATENT DOCUMENTS

| | | | |
|---|---|---|---|
| 5,135,264 A * | 8/1992 | Elliott-Moore | 285/2 |
| 5,417,242 A * | 5/1995 | Goncze | 137/625.17 |
| 5,896,857 A * | 4/1999 | Hely et al. | 128/205.24 |
| 5,937,851 A * | 8/1999 | Serowski et al. | 128/202.27 |
| 6,112,745 A | 9/2000 | Lang | |
| 6,189,532 B1* | 2/2001 | Hely et al. | 128/205.24 |
| 7,174,893 B2* | 2/2007 | Walker et al. | 128/206.21 |
| 7,559,326 B2* | 7/2009 | Smith et al. | 128/207.12 |
| 8,028,692 B2* | 10/2011 | Ho | 128/200.24 |

FOREIGN PATENT DOCUMENTS

DE 198 40 760 A1 9/2000

* cited by examiner

*Primary Examiner* — Steven Douglas
(74) *Attorney, Agent, or Firm* — McGlew and Tuttle, P.C.

(57) ABSTRACT

A device for releasing breathing gas establishes constant flow conditions for the breathing gas being discharged. An annular connection element (6) is provided between an outer part (2) and an inner part (4), and a discharge gap (7) is formed between the connection element (6) and the outer part (2).

21 Claims, 4 Drawing Sheets

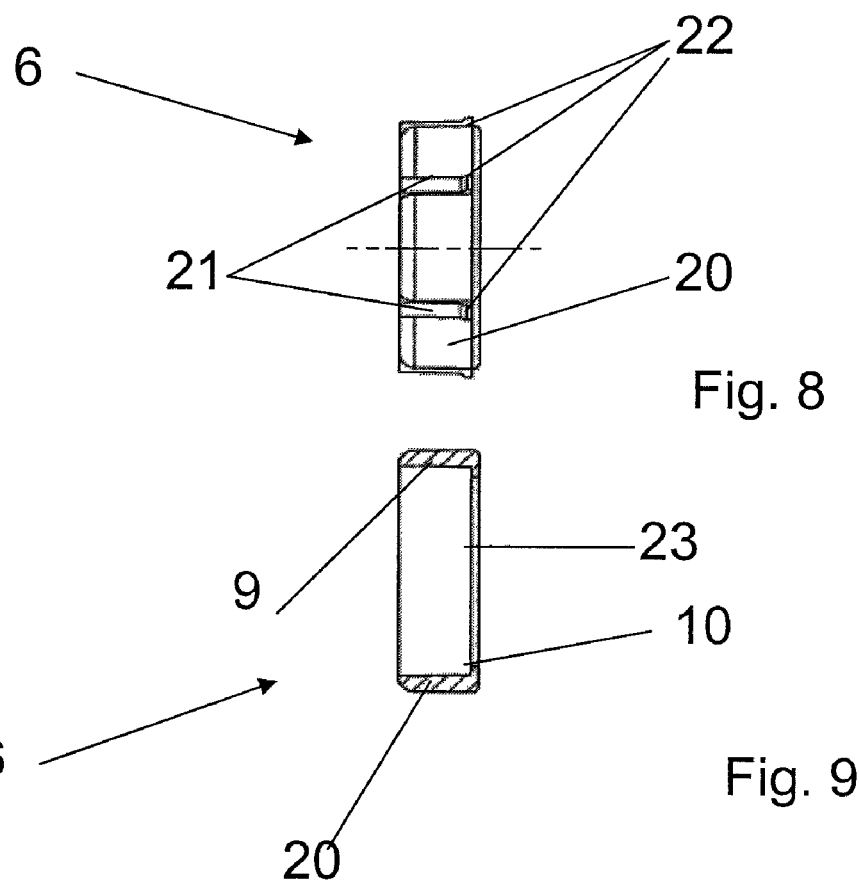

DEVICE FOR RELEASING BREATHING GAS

CROSS REFERENCE TO RELATED APPLICATIONS

This application claims the benefit of priority under 35 U.S.C. §119 of German Patent Application DE 10 2007 052 898.3 filed Nov. 7, 2007, the entire contents of which are incorporated herein by reference.

FIELD OF THE INVENTION

The present invention pertains to a device for releasing breathing gas.

BACKGROUND OF THE INVENTION

A device of the type is known from DE 198 40 760 A1 (corresponding to U.S. Pat. No. 6,112,745). Such devices are used in conjunction with so-called CPAP respirators (Continuous Positive Airway Pressure), with which a constant airway pressure, which assists the spontaneous breathing, is set for the patient, e.g., in connection with the treatment of sleep apnea.

The prior-art device comprises an outer part and an inner part, which are rotatable in relation to one another and are fitted together by means of a snap-in connection. The external diameter of the inner part and the internal diameter of the outer part are selected to be such that an annular gap is formed, through which the breathing gas can flow off into the environment from the inner area. The two free ends of the prior-art device are connected to a breathing mask, on the one hand, and to a flexible breathing tube, on the other hand, and the torsional moments possibly developing at the flexible breathing tube can be extensively eliminated due to the rotatability of the outer part in relation to the inner part.

The diameters of the outer part and of the inner part, which form the annular gap, must be exactly coordinated with one another in order for a sufficiently high pressure to be able to be built up in the flexible breathing tube, on the one hand, and for flow noises due to the breathing gas flowing out of the annular gap to be reduced to a minimum, on the other hand. The width of the annular gap changes due to manufacturing tolerances, and it is also not possible to prevent the inner part from being in contact with the outer part on one side, as a result of which an asymmetrical annular gap becomes established, which has an adverse effect on the pressure conditions and the flow noises.

SUMMARY OF THE INVENTION

The basic object of the present invention is to improve a device of the type such that constant flow conditions will become established for the breathing gas being discharged from the annular gap.

According to the invention, a device is provided for releasing breathing gas. The device is provided with an outer part, with an inner part, which has a cylindrical sliding surface, and with an annular connection element, which has a mounting sleeve, which is designed corresponding to the cylindrical sliding surface of the inner part. The mounting sleeve is located on the inside. A stop is provided for fixing the inner part. A discharge gap is formed between the connection element and the outer part.

The advantage of the device according to the present invention is that an annular connection element is additionally provided, which forms a constant discharge gap together with the outer part, on the one hand, and has a mounting sleeve for the inner part, on the other hand. Due to the inner part being fastened by means of the mounting sleeve, the rotary motion of the inner part is uncoupled in relation to the outer part. Due to the connection element, there are no reactions when the inner part is being moved in relation to the outer part, and the geometry of the discharge gap remains unchanged.

The outer contour of the connection element can be designed in respect to the inner contour of the outer part such that optimal flow conditions will become established while the lowest possible noise is generated. The length and width of the discharge gap can now be selected to be such that acceptable flow values will become established.

A reproducible gap width of the discharge gap can be advantageously embodied by means of spacing elements arranged on the circumference of the connection element.

The connection element has, in addition to the mounting sleeve, a stop for the sliding surface of the inner part.

It is especially advantageous to fix the connection element such that it is secured against rotation in relation to the outer part by the spacing elements having snap-in pins, which snap into groove-like depressions on the outer part. The means securing against rotation can now be embodied such that the spacing elements are pushed into grooves belonging to them on the outer part, as a result of which a preferential position of the connection element is obtained in relation to the outer part. However, it is also possible, as an alternative, to achieve the securing against rotation solely by the frictional engagement of the snap-in pins within the groove-like depressions. Another possibility of securing against rotation is to bond or weld the connection element to the outer part.

An improvement of the centering of the inner part in relation to the outer part is obtained by means of a guide element, which is connected to the inner part and which is inserted into a contact surface designed correspondingly thereto on the outer part. The guide element adjoins the sliding surface of the inner part via the webs. The guide element in conjunction with the contact surface as well as the sliding surface in conjunction with the stop form together an axial guide of the inner part in relation to the outer part.

An exemplary embodiment of the present invention is shown in the drawings and will be explained in more detail below. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

BRIEF DESCRIPTION OF THE DRAWINGS

In the drawings:

FIG. 8 is a side view showing a section connection element; and

FIG. 9 is a longitudinal sectional view showing the connection element according to FIG. 8.

DESCRIPTION OF THE PREFERRED EMBODIMENTS

Figure 1:
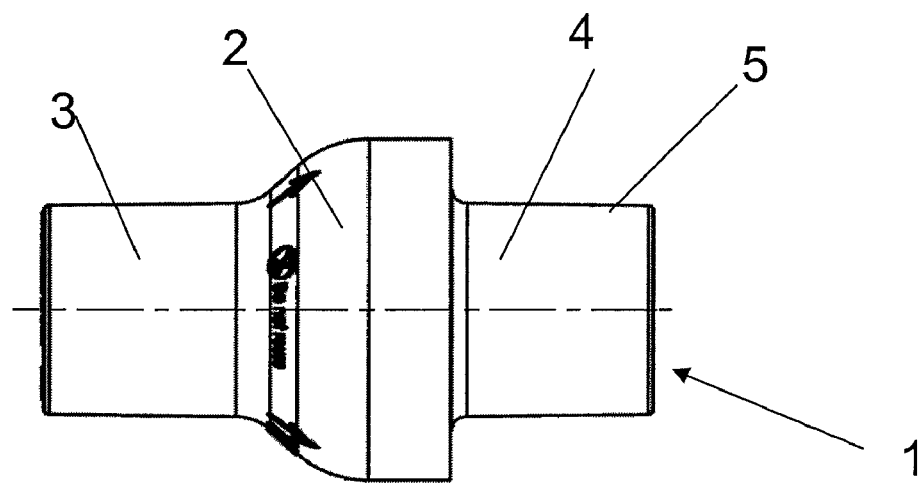
FIG. 1 is a side view showing a device according to the present invention for releasing breathing gas.

Referring to the drawings in particular, FIG. 1 schematically shows a side view of a device 1 according to the present invention for releasing breathing gas, containing an outer part 2 with a mask port 3 and an inner part 4 with a flexible tube port 5.

Figure 2:
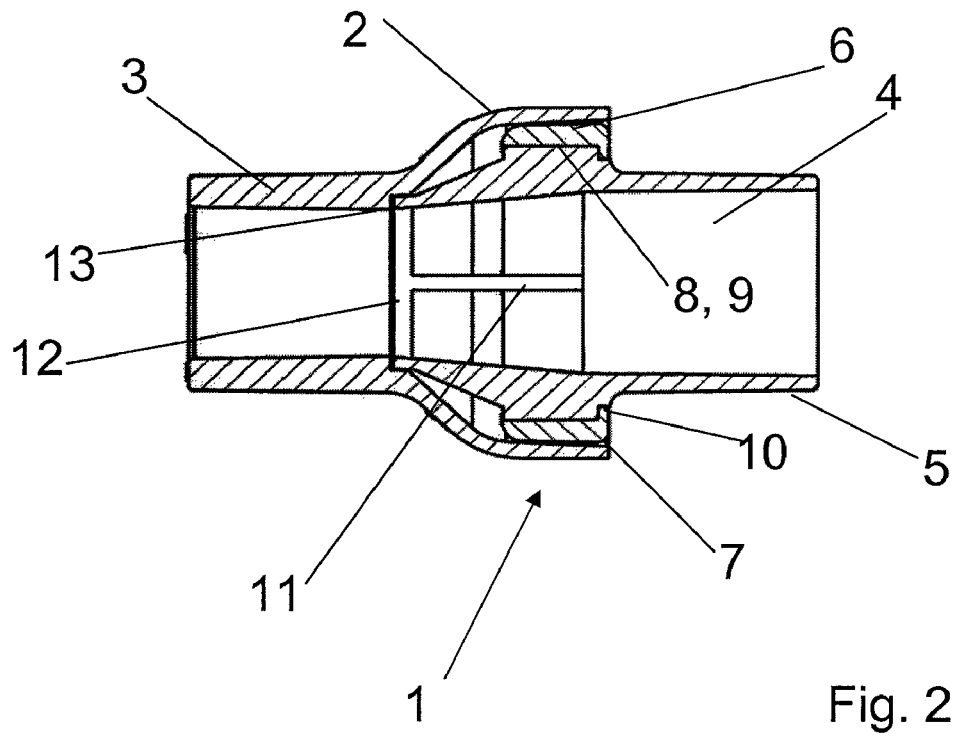
FIG. 2 is a sectional view showing the device according to FIG. 1 in a longitudinal section.

FIG. 2 shows the device 1 according to FIG. 1 in a longitudinal section. Identical components are designated by the same reference numbers as in FIG. 1. The inner part 4 is fastened rotatably by means of a connection element 6 within the outer part 2. An annular discharge gap 7 for breathing gas is formed between the connection element 6 and the outer part 2.

The inner part 4 has a cylindrical sliding surface 8, which is located within a mounting sleeve 9 having a design corresponding thereto with a stop 10. The sliding surface 8 is adjoined via webs 11 by a disk-shaped guide segment 12, which is in contact with a contact surface 13 of the outer part 2. The contact surface 13 and the stop 10 limit the axial clearance of the inner part 4 in relation to the outer part 2.

Figure 3:
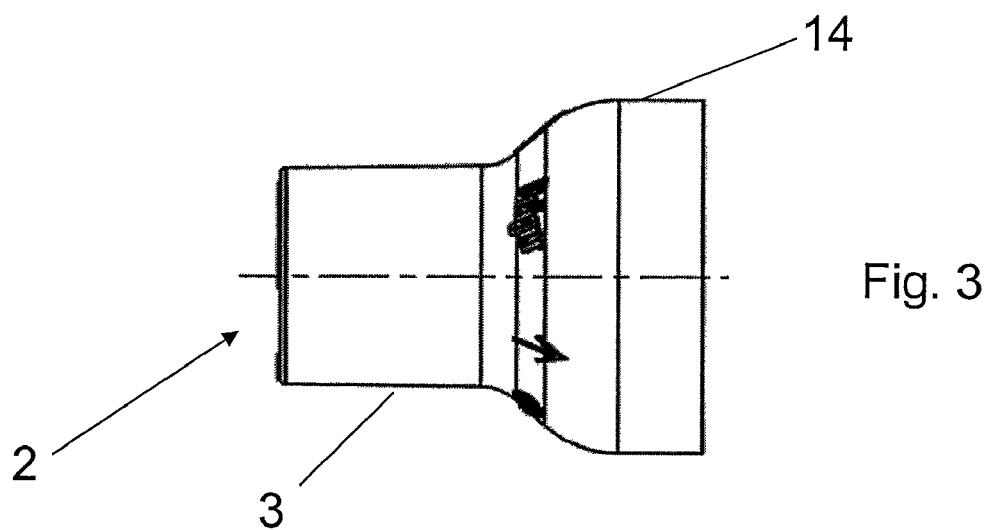
FIG. 3 is a side view showing an outer part.
Figure 4:
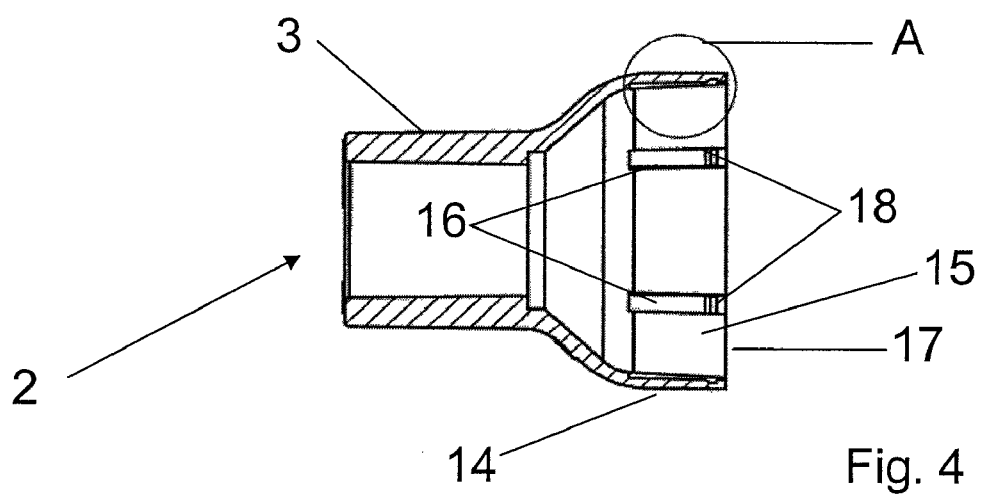
FIG. 4 is a longitudinal sectional view showing the outer part according to FIG. 3.

FIG. 3 illustrates a side view of the outer part 2. The mask port 3 is designed such that it comprises a 22-mm outer cone and a 15-mm inner cone arranged therein, as can be determined from FIG. 4. FIG. 4 shows a longitudinal section through the outer part 2. The mask port 3 with the external diameter of 22 mm expands stepwise to a discharge section 14 with an external diameter of 36 mm. On its inner surface 15, the discharge section 14 has axially extending grooves 16, which are provided with locking grooves 18 towards the front side 17.

Figure 5:
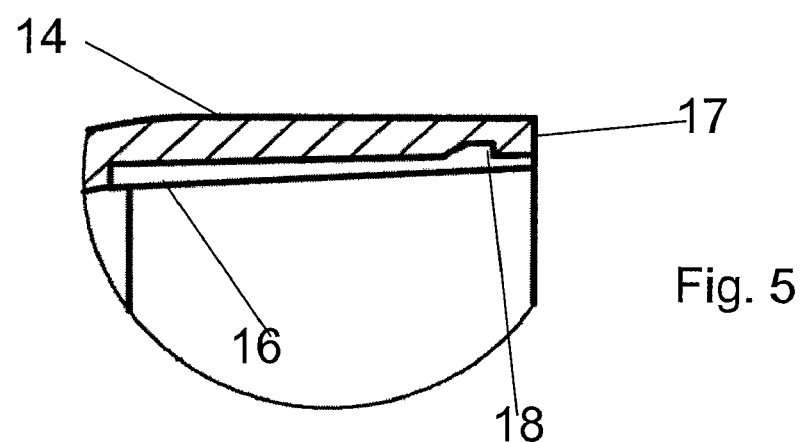
FIG. 5 is detail A according to FIG. 4.

FIG. 5 shows an enlarged view of detail A according to FIG. 4 in the area of groove 16 and the locking groove 18.

Figure 6:
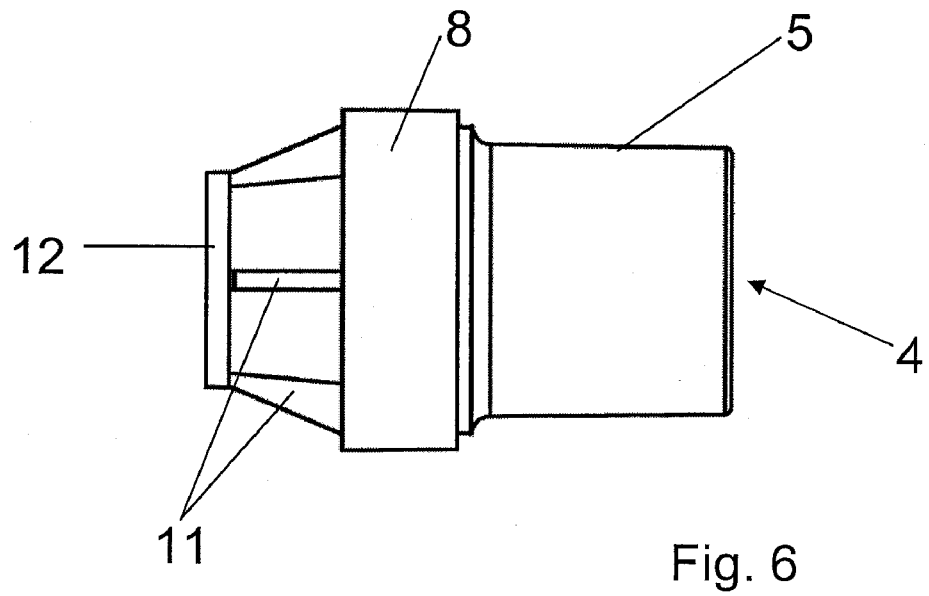
FIG. 6 is a side view showing an inner part.
Figure 7:
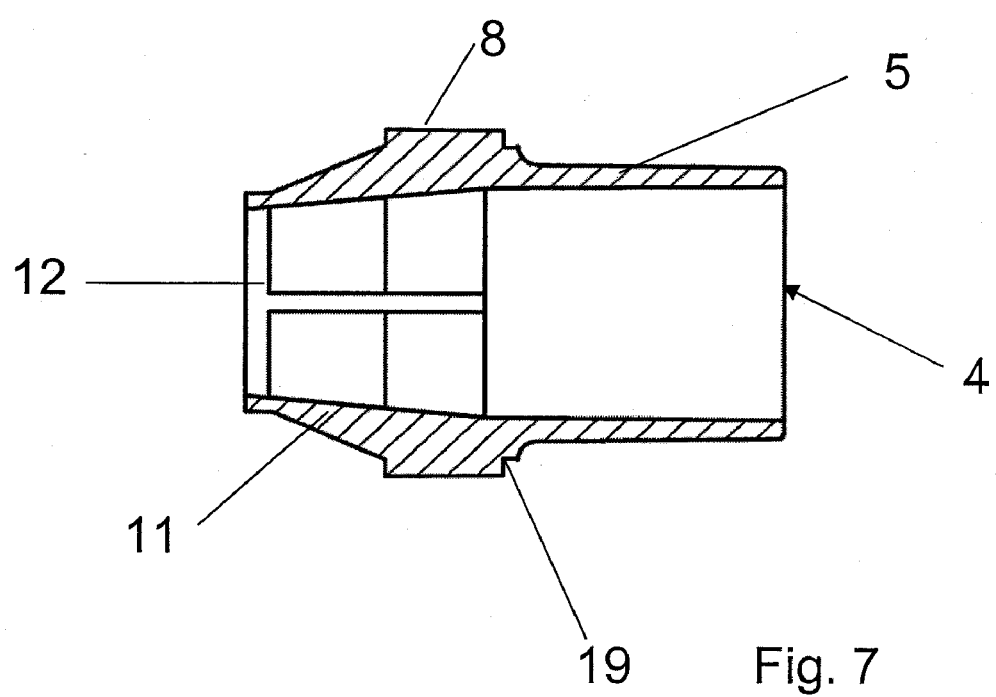
FIG. 7 is a longitudinal sectional view showing the inner part according to FIG. 6.

FIG. 6 shows a side view of the inner part 4. The inner part 4 is shown in a longitudinal section in FIG. 7. The sliding surface 8 has a shoulder 19, which is in contact with the stop 10 of connection element 6.

FIG. 8 shows a side view of the connection element 6. Axially extending, bar-shaped spacing elements 21, which extend axially, are designed corresponding to the grooves 16 of the outer part 2, FIG. 4, and have snap-in pins 22 directed towards the front side 17, are arranged on the outer side 20 of the connection element 6.

FIG. 9 illustrates a longitudinal section of the connection element 6 according to FIG. 8. An opening 23 for inserting the inner part 2 is located in the area of stop 10.

To mount the device according to the present invention, the inner part 4 is at first inserted into the connection element 6 such that the sliding surface 8 is located within the mounting sleeve 9 and the stop 10 strikes the shoulder 19. The inner part 4 is then inserted together with the connection element 6 into the outer part 2 such that the spacing elements 21 are located within the grooves 16. When the snap-in pins 22 have snapped into the locking grooves 18, the inner part 4 is nondetachably connected to the outer part 2 and the discharge gap 7 is formed between the connection element 6 and the outer part 2.

While a specific embodiment of the invention has been shown and described in detail to illustrate the application of the principles of the invention, it will be understood that the invention may be embodied otherwise without departing from such principles.

What is claimed is:

1. A device for releasing breathing gas, the device comprising:
   an outer part;
   an inner part having a cylindrical sliding surface extending in an axial direction of said inner part; and
   an annular connection element with a mounting sleeve receiving said cylindrical sliding surface of said inner part to define a rotational sliding connection of said inner part to said annular connection element, said annular connection element having an annular stop fixing said inner part, said stop defining an inner part removal stop means for preventing axial removal of said inner part relative to said stop said, said annular stop extending in said axial direction, connection element and said outer part together forming a discharge gap between said connection element and said outer part.

2. A device in accordance with claim 1, wherein said outer part and said annular connection element cooperate to provide locking means for locking said annular connection element in said outer part.

3. A device in accordance with claim 2, wherein said locking means comprises spacing elements at an outer surface of said annular connection element.

4. A device in accordance with claim 3, wherein said spacing elements have snap-in pins at the outer surface of said annular connection element, said locking means further comprising grooves on an inner surface of said outer part, said grooves comprising locking grooves, wherein said snap-in pins snap into said locking grooves, whereby said inner part is nondetachably connected to said outer part.

5. A device in accordance with claim 1, wherein said inner part has a guide segment, which is connected via webs to an area of said sliding surface.

6. A device in accordance with claim 5, wherein said outer part has a contact surface corresponding to said guide segment.

7. A mount device for releasing breathing gas from a supply having a flexible tube to a breathing mask, the device comprising:
   an annular outer part with a mask port;
   an annular inner part having cylindrical sliding surface extending in an axial direction of said inner part and a flexible tube port; and
   an annular connection element with a mounting sleeve having a cooperating surface corresponding to said cylindrical sliding surface of said inner part for allowing rotational sliding of said inner part relative to said annular connection element, said annular connection element having an annular stop for fixing said inner part in an axial direction relative to said annular connection element and said outer part, said annular stop extending in an axial direction, and said annular connection element cooperating to provide locking means for locking said annular connection element in said outer part, said connection element and said outer part together forming a discharge gap between said connection element and said outer part.

8. A device in accordance with claim 7, wherein said discharge gap is formed by spacing elements between said annular connection element and said outer part.

9. A device in accordance with claim 8, wherein said spacing elements form part of said locking means and are positioned to fix said annular connection element in relation to said outer part in such a way that said annular connection element is secured against rotation.

10. A device in accordance with claim 8, wherein said spacing elements have snap-in pins that can be connected to said outer part.

11. A device in accordance with claim 7, wherein said inner part has a guide segment, which is connected via webs to an area of said sliding surface.

12. A device in accordance with claim 11, wherein said outer part has a contact surface corresponding to said guide segment.

13. A device in accordance with claim 7, wherein said locking means comprises spacing elements and snap-in pins at an outer surface of said annular connection element and grooves provided with locking grooves on an inner surface of said outer part, wherein said snap-in pins snap into said locking grooves whereby said inner part is nondetachably connected to said outer part and said discharge gap is formed between said annular connection element and said outer part.

14. A method of providing a mount device for releasing breathing gas from a supply having a flexible tube to a breathing mask, the method comprising the steps of:
providing an annular outer part with a mask port;
providing an annular inner part having a cylindrical sliding surface extending in an axial direction of said inner part, a shoulder and a flexible tube port;
providing an annular connection element with a mounting sleeve having a surface receiving said cylindrical sliding surface of said inner part to define a rotational sliding connection of said inner part to said annular connection element, said annular connection element having an annular stop, said annular connection element cooperating with said outer part to provide locking means for locking said annular connection element in said outer part;
inserting said inner part into said annular connection element such that said sliding surface is located within said mounting sleeve and said inner part is fixed, relative to said stop, in an axial direction via said stop said annular stop extends in said axial direction and;
inserting said inner part together with said connection element into said outer part for locking said connection element to said outer part whereby said annular connection element and said outer part together form a discharge gap between said annular connection element and said outer part.

15. A method in accordance with claim 14, wherein said discharge gap is formed by spacing elements between said annular connection element and said outer part.

16. A method in accordance with claim 15, wherein said spacing elements form part of said locking means and are positioned to fix said annular connection element in relation to said outer part in such a way that said annular connection element is secured against rotation.

17. A method in accordance with claim 16, wherein said spacing elements have snap-in pins that can be connected to said outer part.

18. A method in accordance with claim 17, wherein said inner part has a guide segment, which is connected via webs to an area of said sliding surface.

19. A method in accordance with claim 18, wherein said outer part has a contact surface corresponding to said guide segment.

20. A method in accordance with claim 14, wherein said locking means comprises spacing elements and snap-in pins at an outer surface of said annular connection element and grooves provided with locking grooves on an inner surface of said outer part, wherein said snap-in pins snap into said locking grooves whereby said inner part is nondetachably connected to said outer part.

21. A device in accordance with claim 1, wherein said outer part and said stop cooperate to fix said inner part in an axial direction relative to said outer part and said annular connection element.

\* \* \* \* \*